United States Patent [19]

Newsome

[11] Patent Number: 6,090,927

[45] Date of Patent: Jul. 18, 2000

[54] INTERMEDIATES FOR PREPARING PYRAZOLE DERIVATIVES

[75] Inventor: Peter Wyatt Newsome, Chapel Hill, N.C.

[73] Assignee: Rhone-Poulenc Inc., Research Triangle Park, N.C.

[21] Appl. No.: 09/249,798

[22] Filed: Feb. 16, 1999

Related U.S. Application Data

[62] Division of application No. 08/815,848, Mar. 12, 1997, Pat. No. 5,907,041.

[51] Int. Cl.$^7$ .............................. C09B 39/00; C09B 41/00
[52] U.S. Cl. .............................................. 534/651; 534/581
[58] Field of Search ...................................... 534/651, 581

[56] References Cited

U.S. PATENT DOCUMENTS

| | | | |
|---|---|---|---|
| 2,978,480 | 4/1961 | Luckenbaugh | 558/437 |
| 3,140,226 | 7/1964 | Stephens et al. | 514/520 |
| 4,933,436 | 6/1990 | Wolff et al. | 534/581 |
| 5,232,940 | 8/1993 | Hatton et al. | 514/407 |
| 5,236,938 | 8/1993 | Huang et al. | 514/341 |

FOREIGN PATENT DOCUMENTS

| | | |
|---|---|---|
| 0295117 | 12/1988 | European Pat. Off. . |
| 0385809 | 9/1990 | European Pat. Off. . |
| 0403300 | 12/1990 | European Pat. Off. . |
| 0679650 | 11/1995 | European Pat. Off. . |
| 2928136 | 1/1981 | Germany . |
| 3602524 | 7/1987 | Germany . |
| 19511269 | 10/1995 | Germany . |
| 87/03781 | 7/1987 | WIPO . |
| 93/06089 | 4/1993 | WIPO . |
| 94/21606 | 9/1994 | WIPO . |

OTHER PUBLICATIONS

Phillips, *Organic Reactions*, vol. 10, ed. Adams et al, John Wiley & Sons, Inc., New York, Chapter 2, pp. 143–178 (1959).

Eastman et al, *Journal of the American Chemical Society*, vol. 70, No. 3, pp. 962–964 (1948).

Heckendorn, *Bull. Soc. Chim. Belg.*, vol. 95, No. 11, pp. 921–943 (1986).

Redman et al, *Journal of the Chemical Society, Perkin Transactions II*, pp. 1135–1144 (1978).

*Primary Examiner*—Alan L. Rotman
*Attorney, Agent, or Firm*—Burns, Doane, Swecker & Mathis, L.L.P.

[57] ABSTRACT

The invention relates to novel intermediates in a process for preparing compounds having the formula:

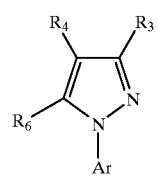

(IV)

wherein $R_3$, $R_4$, $R_6$ and Ar are as defined in the description, by reaction of a compound of formula (I) with a compound of formula (II) according to the following reaction scheme:

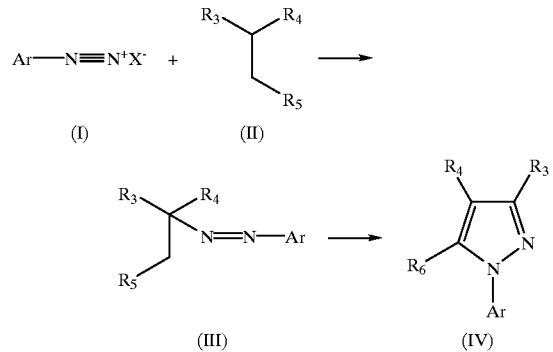

The compounds of formula (IV) are useful as pesticides.

1 Claim, No Drawings

INTERMEDIATES FOR PREPARING PYRAZOLE DERIVATIVES

CROSS-REFERENCE TO RELATED APPLICATION

This application is a divisional of U.S. application No. 08/815,848, filed Mar. 12, 1997, U.S. Pat. No. 5,907,041.

BACKGROUND OF THE INVENTION

1. Field of the Invention

The instant invention is directed to novel intermediates in a new process for manufacturing pesticidally active materials. More particularly, the instant invention is directed to intermediates in a process for manufacturing 1-aryl substituted pyrazoles.

2. Background Art

Many manufacturing processes have been described in the literature for preparing such derivatives, for example in International Patent Publication Nos. WO87/03781, WO93/06089 and WO94/21606; in European Patent Publication Nos. 0295117, 0403300, 0385809 and 0679650; U.S. Pat. Nos. 5,232,940 and 5,236,938; and German Published Patent Application No. 19511269.

The Japp-Klingemann reaction, reviewed in *Org. React.*, Vol. 10, pages 143–178 (1959), known in the literature since 1887, is a process by which phenyl azo compounds are formed from the reaction of diazonium salts with active methylene compounds. Typically the phenyl azo compound is not isolated, but is reacted in situ with base resulting in loss of a leaving group and formation of the corresponding hydrazone. When the phenyl azo intermediate is properly substituted, a spontaneous cyclization reaction occurs giving a 3,5-disubstituted-4-protio-pyrazole, that is, a 3,5-disubstituted-4-unsubstituted pyrazole. If a 3,4,5-trisubstituted pyrazole is desired, further manipulation is required in subsequent steps.

OBJECTS AND SUMMARY OF THE INVENTION

An object of the instant invention is to provide a new manufacturing process for preparing arylpyrazole derivatives.

Another object of the instant invention is to provide a simple manufacturing process, if possible, more simple than the existing process.

These objects are met in whole or in part by the instant invention.

This invention provides a new and more efficient process for the direct preparation of 3,4,5-trisubstituted-1-arylpyrazoles. Surprisingly, it has been found that the pyrazole ring cyclization of certain aryl azo intermediates proceeds such that the leaving group (normally lost in these type of reactions) is reincorporated into the pyrazole at C-4 thus giving immediate access to 3,4,5-trisubstitated-1-arylpyrazoles. This offers advantages in reducing the number of reaction steps required to produce the desired pesticidally active 3,4,5-trisubstituted-1-arylpyrazole derivatives, which in turn means less waste chemical may be generated when manufacturing such compounds; and less energy may be needed. This also helps to reduce the manufacturing cost of the pesticidally active 1-aryl pyrazole derivatives.

The invention thus provides a process for preparing 1-arylpyrazoles according to the following reaction scheme:

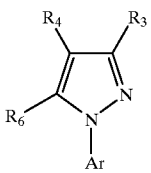

(IV)

wherein:
Ar is optionally substituted phenyl or optionally substituted pyridyl;
X is a compatible anion;
$R_3$ represents —C(O)$R_8$, —CN, —CO$_2$H, —C(O)NHR$_8$, —CHO, —C(O)CO$_2$R$_8$, —S(O)$_m$R$_8$, —C(O)CH$_2$Het, Het, —C(O)CH$_2$R$_9$, —C(O)alkyl, —C(O)haloalkyl, —C(O)styryl, halogen, —C(O)OR$_8$, —P(O)(OR$_8$)$_2$, —P(S)(OR$_8$)$_2$, —NO$_2$, R$_9$ or —S(O)$_m$styryl;
$R_4$ is as defined for $R_3$ excluding —CN and halogen;
m is 0, 1, or 2;
$R_5$ is —CN, —C(O)OR$_8$ or —C(O)-alkyl;
$R_6$ is —NH$_2$, —OH, or alkyl;
$R_8$ is alkyl, haloalkyl, R$_9$ or Het;
Het represents a 5- or 6-membered heterocyclic ring, said ring having from one to three ring heteroatoms which are the same or different selected from the group consisting of nitrogen, sulfur and oxygen, each carbon atom of said ring being unsubstituted or being substituted by halogen, alkyl, haloalkyl, alkoxy, haloalkoxy, cyano, nitro, amino, N-alkylamino, N,N-dialkylamino, OH, —S(O)$_m$alkyl or —S(O)$_m$haloalkyl; and
$R_9$ represents phenyl optionally substituted by one or more members selected from the group consisting of halogen, alkyl, haloalkyl, alkoxy, haloalkoxy, cyano, nitro, amino, N-alkylamino, N,N-dialkylamino, —OH, —S(O)$_m$alkyl, and —S(O)$_m$haloalkyl.

DETAILED DESCRIPTION OF THE INVENTION AND PREFERRED EMBODIMENTS

In the specification the following terms have the general meanings given below:

"alkyl" is branched or straight chain alkyl having from 1 to 6 carbon atoms;

"haloalkyl" is branched or straight chain alkyl having from 1 to 6 carbon atoms, bearing one or more halogen which are the same or different;

"alkoxy" is branched or straight chain alkoxy having from 1 to 6 carbon atoms;

"haloalkoxy" is branched or straight chain alkoxy having from 1 to 6 carbon atoms, bearing one or more halogen which are the same or different;

"halogen" means fluorine, chlorine, bromine or iodine.

In the definition above it will be understood that $R_4$ cannot represent —CN or halogen because in formula (III) above, —CN or halogen cannot migrate to the adjacent carbon atom in the rearrangement step to give the compound of formula (IV) above.

X can be any anion compatible with the reaction conditions prevailing. Examples of suitable groups include (HSO$_4$), halogen, (BF$_4$), (ZnCl$_3$) and (CoCl$_3$). Preferably X is halogen or (HSO$_4$).

When Ar is phenyl, it has from 0 to 5 substituents. When Ar is pyridyl, it has from 0 to 4 substituents. Preferably, Ar has from 1 to 3 substituents. In any event, the optional Ar substituents are preferably selected from the group consisting of halogen, CN, $NO_2$, haloalkyl, haloalkoxy, $S(O)_mCF_3$, $SF_5$ and $R_{10}$ wherein m is as defined above and $R_{10}$ is as defined below.

Preferably Ar is a group having the formula

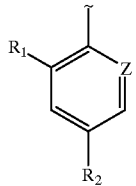

wherein:

Z represents a trivalent nitrogen atom or a C—$R_7$ radical, the other three valences of the carbon atom forming part of the aromatic ring;

$R_1$ and $R_7$ represent, independently of each other, a hydrogen or halogen atom, or CN or $NO_2$;

$R_2$ represents halogen, haloalkyl, haloalkoxy, $S(O)_mCF_3$, $SF_5$ or $R_{10}$;

and $R_{10}$ is phenyl optionally having from one to five substituents selected from the group consisting of halogen; alkyl; haloalkyl; cyanoalkyl; cyano; nitro; amino; hydrazino; alkoxy; haloalkoxy; haloalkylcarbonyl; formyl; alkylcarbonyl; thiocarbamoyl; carbamoyl; alkoxycarbonyl; $SF_5$; and $R_8S(O)_m$ (preferably the 4-position substituent being halogen, haloalkyl or haloalkoxy); two adjacent phenyl substituents being optionally joined together form a 1,3-butadienylene (—CH=CH—CH=CH—), methylenedioxy (—O—$CH_2$—O—) or halomethylenedioxy (e.g., —O—$CF_2$—O—) group so as to form a cyclic ring vicinal to the phenyl ring.

The following are also preferred embodiments of the invention, especially when Ar is one of the preferred groups depicted above:

$R_3$ is —CN or —$COR_8$; and/or $R_4$ is —$S(O)_mR_9$, —$S(O)_m$alkyl or —$S(O)_m$haloalkyl; and/or $R_5$ is —CN; and/or $R_6$ is —$NH_2$.

The following value of the various substituents provide representative compounds of formulae (I) to (IV) above. In the Table that follows "Ph" means phenyl; "Pyr" means pyridyl; "Et" means ethyl.

| Ar | X | $R_3$ | $R_4$ | $R_5$ | $R_6$ |
|---|---|---|---|---|---|
| 2,6-$Cl_2$-4-$CF_3$ Ph | $HSO_4$ | $COCH_3$ | $SO_2$(4-Cl Ph) | CN | $NH_2$ |
| 2,6-$Cl_2$-4-$CF_3$ Ph | $HSO_4$ | CN | $SO_2$(4-Cl Ph) | CN | $NH_2$ |
| 2,6-$Cl_2$-4-$CF_3$ Ph | $HSO_4$ | CN | $CO_2$Et | CN | $NH_2$ |
| 2,6-$Cl_2$-4-$CF_3$ Ph | $HSO_4$ | CN | $SOCF_3$ | CN | $NH_2$ |
| 2,6-$Cl_2$-4-$CF_3$ Ph | $HSO_4$ | CN | $SOCH_3$ | CN | $NH_2$ |
| 2,6-$Cl_2$-4-$OCF_3$ Ph | Cl | Cl | $SOCF_3$ | CN | $NH_2$ |
| 2,6-$Cl_2$-4-$CF_3$ Ph | $HSO_4$ | CN | SOEt | CN | $NH_2$ |
| 2,6-$Cl_2$-4-$CF_3$ Ph | $HSO_4$ | CN | $P(O)(OEt)_2$ | CN | $NH_2$ |
| 2,6-$Cl_2$-4-$CF_3$ Ph | Cl | CN | $SO_2CF_3$ | CN | $NH_2$ |
| 2,6-$Cl_2$-4-$CF_3$ Ph | $HSO_4$ | $SO(4-Cl Ph)$ | $COCH_3$ | CN | $NH_2$ |
| 2,6-$Cl_2$-4-$CF_3$ Ph | $HSO_4$ | CN | $COCF_3$ | CN | $NH_2$ |
| 2,6-$Cl_2$-4-$CF_3$ Ph | $HSO_4$ | CN | $NO_2$ | CN | $NH_2$ |
| 2,6-$Cl_2$-4-$CF_3$ Ph | $HSO_4$ | $NO_2$ | $COCH_3$ | CN | $NH_2$ |
| 2,6-$Cl_2$-4-$CF_3$ Ph | $HSO_4$ | $SO_2$(2-thienyl) | $COCH_3$ | CN | $NH_2$ |
| 2,6-$Cl_2$-4-$CF_3$ Ph | $HSO_4$ | $COCH_3$ | $SO_2$(2-thienyl) | CN | $NH_2$ |
| 2,6-$Cl_2$-4-(4-Cl Ph) Ph | $HSO_4$ | CN | $SOCF_3$ | CN | $NH_2$ |
| 2,6-$Cl_2$-4-$CF_3$ Ph | $HSO_4$ | Br | $COCH_3$ | CN | $NH_2$ |
| 2,6-$Cl_2$-4-$CF_3$ Ph | $HSO_4$ | Br | COPh | CN | $NH_2$ |
| 2,6-$Cl_2$-4-$CF_3$ Ph | $HSO_4$ | CN | CO(2-furyl) | CN | $NH_2$ |
| 2,6-$Cl_2$-4-$CF_3$ Ph | $HSO_4$ | CN | $SOCF_3$ | CN | $NH_2$ |
| 2,6-$Cl_2$-4-$SF_5$ Ph | $HSO_4$ | $COCH_3$ | $SO_2$(4-Cl Ph) | CN | $NH_2$ |
| 2,6-$Cl_2$-4-$SF_5$ Ph | $HSO_4$ | CN | $SO_2$(4-Cl Ph) | CN | $NH_2$ |
| 2,6-$Cl_2$-4-$SF_5$ Ph | $HSO_4$ | CN | $CO_2$Et | CN | $NH_2$ |
| 2,6-$Cl_2$-4-$SF_5$ Ph | $HSO_4$ | CN | $SOCF_3$ | CN | $NH_2$ |
| 2,6-$Cl_2$-4-$SF_5$ Ph | $HSO_4$ | CN | $SOCH_3$ | CN | $NH_2$ |
| 2,6-$Cl_2$-4-$SF_5$ Ph | Cl | Cl | $SOCF_3$ | CN | $NH_2$ |
| 2,6-$Cl_2$-4-$SF_5$ Ph | $HSO_4$ | CN | SOEt | CN | $NH_2$ |
| 2,6-$Cl_2$-4-$SF_5$ Ph | $HSO_4$ | CN | $P(O)(OEt)_2$ | CN | $NH_2$ |
| 2,6-$Cl_2$-4-$(4CF_3$ Ph) Ph | $HSO_4$ | CN | $SOCF_3$ | CN | $NH_2$ |
| 2,6-$Cl_2$-4-(4-$OCF_3$ Ph) Ph | $HSO_4$ | CN | $SOCF_3$ | CN | $NH_2$ |
| 2,6-$Cl_2$-4-O Ph | $HSO_4$ | CN | $SOCF_3$ | CN | $NH_2$ |
| 2,6-$Cl_2$-4-(4-$SCF_3$ Ph) Ph | $HSO_4$ | CN | $SOCF_3$ | CN | $NH_2$ |

The process of the invention is generally conducted in two steps, although it may be carried out as a continuous process including the in-situ rearrangement of the compound of formula (III) to give a compound of formula (IV). This in-situ process may be preferred when the process forms part of a manufacturing process, as it may avoid the need for isolation of the intermediate of formula (II).

In the first step the diazonium salt (I) is reacted with a compound (II) in a solvent, with protic solvents such as methanol, ethanol and acetic acid being preferred. The reaction is performed, optionally in the presence of a base, at a temperature between about 0° and about 120° C., preferably between about 0 and about 25° C., to give the azo product (III). When base is used in this step, it can be organic such as pyridine or triethylamine, or inorganic such as potassium carbonate or sodium hydroxide. When used, the amount of base is generally from about 1 to about 25 equivalents [based on the mole equivalents of the compound of formula (I)], with about 1 to 5 equivalents being preferred.

In the second step of the reaction sequence, the azo compound (III) is dissolved in a suitable solvent and optionally subjected to up to about 20 equivalents of a base, preferably up to about 5 equivalents, to give the rearranged pyrazole of formula (IV). The reaction temperature for this step is from about 0 to about 120° C., preferably from about 0 to about 25° C. The solvent can be protic such as methanol, ethanol or acetic acid, or preferably the solvent can be aprotic, such as dichloromethane, tetrahydrofuran, or toluene. Suitable bases may be organic (such as pyridine, triethylamine, or piperidine), inorganic (such as sodium hydroxide, potassium carbonate, sodium hydride) or organometallic (such as potassium t-butoxide, sodium methoxide, lithium diisopropylamide), with organic or organometallic bases being preferred.

The compound of formula (III) above is generally present in a molar excess. Preferably from about 1 to about 2 moles of the compound of formula (III) are present, more preferably from about 1.05 to about 1.1 moles.

Compounds of formula (III) in which Ar, $R_3$, $R_4$ and $R_5$ are as defined above, provided that when $R_3$ and $R_5$ are both cyano $R_4$ is not —$C(O)OR_8$, are novel and thus constitute a feature of the present invention.

Compounds of formula (II) may be prepared by the reaction of a compound of formula (V):

$$R_3—CH_2R_4 \hspace{4cm} \text{(V)}$$

wherein $R_3$ and $R_4$ are as defined above with a compound of the formula $R_5CH_2L$ wherein $R_5$ is as defined above and L is a leaving group, in the presence of a base. Examples of suitable leaving groups include halogen and tosylate (preferably halogen). The base is generally a strong base (e.g. sodium hydride or n-butyl lithium) and the reaction is generally performed in an aprotic solvent (e.g. tetrahydrofuran) at a temperature from about −78° C. to about 0° C. Compounds of formula (II), in which $R_5$ is cyano and $R_3$ and $R_4$ are as defined above, provided that when $R_3$ is —CN then $R_4$ is not —C(O)OR$_8$, are also novel and thus constitute a further feature of the present invention.

The following non-limiting examples illustrate the invention.

EXAMPLE 1
Preparation of 3-(4-chlorophenylsulfonyl)-4-cyanobutan-2-one

To a 300 mL reaction flask was added 2.4 g (59.3 mmole) sodium hydride (60% dispersion in oil) and 10 mL hexanes. The hexanes were removed by pipette and replaced by 60 mL dry tetrahydrofuran (THF). The suspension was cooled to −15° C. and a solution of 12.0 g (51.6 mmole) 4-chlorophenylsulfonyl acetone in 50 mL THF was added via addition funnel over 20 minutes maintaining the reaction temperature below −12° C. The resulting yellow solution was removed from the cold bath and stirred at room temperature for 30 min. The solution was recooled to −5° C. and 3.8 mL (54.1 mmole) bromoacetonitrile was added dropwise via addition funnel. After 5 min, the reaction mixture was removed from the cold bath and stirred at room temperature overnight. The reaction was quenched with 1 mL of saturated ammonium chloride and transferred with 100 mL of dichloromethane to a separatory funnel containing 100 mL brine. The organic layer was separated and the aqueous layer was back extracted once with 50 mL more dichloromethane. The combined organics were then dried with sodium sulfate, filtered, concentrated, and chromatographed through a bed of silica gel using 1:1 hexane:dichloromethane. Isolation gave 8.2 g (59% yield) of 3-(4-chlorophenylsulfonyl)4-cyanobutan-2-one, a yellow oil that was 90% pure by HPLC. $^1$H NMR (CDCl$_3$) indicated desired product as the major component: δ7.6 (m, 4H), 4.42 (dd, 1H), 2.78 (m, 2H), 2.48 (s, 3H).

EXAMPLE 2
Preparation of 3-(4-chlorophenylsulfonyl)-3-[(2,6-dichloro-4-trifluoromethlphenyl)azo]-4-cyanobutan-2-one To a 250 mL reaction flask was added 2.0 g (35.7 mmole) potassium hydroxide pellets followed by 30 mL water and 30 mL methanol. To this solution was added 6.9 g (25.5 mmole) of compound 3-(4-chlorophenylsulfonyl)-4-cyanobutan-2-one. Once homogeneous, 23.2 mmole of the hydrogensulfate diazonium salt of 2,6-dichloro-4-trifluoromethylaniline was added in one portion to the reaction medium. After stirring for 45 minutes at room temperature the reaction mixture was worked-up by adding water and dichloromethane. The layers were separated and the organic layer back extracted once with dichloromethane (50 mL). The combined organics were dried (Na$_2$SO$_4$), filtered, concentrated and chromatographed through silica gel using hexane:ethyl acetate mixture. Isolation gave 5.1 g (43%) the title compound as a glassy semi-solid which HPLC indicated was 98% pure and $^1$HNMR indicated as desired product: δ7.6 (m, 4H), 7.65 (s, 2H), 3.3 (dd, 2H), 2.42 (s, 3H).

EXAMPLE 3
Preparation of 3-acetyl-5-amino-4-(4-chlorophenyl)sulfonyl-1-(2,6-dichloro-4-trifluoromethylphenyl)pyrazole Two drops of triethylamine were added to 0.51 g (1.0 mmole) 3-(4-chlorophenylsulfonyl)-3-(2,6-dichloro-4-trifluoromethylphenylazo)-4-cyanobutan-2-one dissolved in 10 mL dichloromethane. After stirring overnight at room temperature, the reaction was worked-up by adding additional dichloromethane and washing with water. The organic layer was separated, dried (Na$_2$SO$_4$), filtered and concentrated to give 0.55 g of the title compound that was 94% pure by HPLC, m.p. 158° C.

EXAMPLE 4
Preparation of 2-(4-chlorophenylsulfonyl)succinonitrile

To a 500 mL reaction flask was added 2.0 g (51.0 mmole) sodium hydride (60% dispersion in oil) and 20 mL hexanes. The hexanes were removed by pipette and replaced by 90 mL dry tetrahydrofuran (THF). The suspension was cooled to 0° C. and a solution of 10.0 g (46.4 mmole) 4-chlorophenylsulfonyl acetonitrile in 90 mL THF was added via addition funnel over 10 minutes maintaining the reaction temperature below 12° C. The resulting solution was removed from the cold bath and stirred at room temperature for 40 min. The solution was recooled to 0° C. and 3.4 mL (48.7 mmole) bromoacetonitrile in 5 mL THF was added dropwise via addition funnel. After 5 minutes, the reaction was removed from the cold bath and stirred at room temperature for two hours. The reaction was quenched with 1 mL of saturated ammonium chloride and concentrated to an oil which was transferred with 150 mL of dichloromethane to a separatory funnel containing 120 mL water. The organic layer was separated and washed once more with 120 mL water and once with 120 mL brine. The organic layer was then dried (Na$_2$SO$_4$), filtered, concentrated, and chromatographed through a bed of silica gel using 85:15 hexane:ethyl acetate. Isolation gave 1.4 g (12% yield) of the title compound as a yellow powder that was 96% pure by HPLC, m.p. 130–137° C.

EXAMPLE 5
Preparation of 2-(4-chlorophenylsulfonyl)-2-(2,6-dichloro-4-trifluoromethyl)phenylazo succinonitrile To a 50 mL reaction flask was added 0.45 g (1.77 mmole) of 2-(4-chlorophenylsulfonyl)succinonitrile in 15 mL methanol. Once homogeneous, 1.61 mmole of the hydrogensulfate diazonium salt of 2,6-dichloro-4-trifluoromethylaniline was added in one portion to the reaction medium. After stirring 45 min at room temperature the reaction mixture was worked-up by adding brine and dichloromethane. The layers were separated and the organic layer was dried (Na$_2$SO$_4$), filtered, concentrated and chromatographed through silica gel using 90:10 hexane:ethyl acetate. Isolation gave 0.33 g (42%) of the title compound, a red crystalline solid which $^{19}$F NMR indicated was over 95% pure, m.p. 45–50° C.

EXAMPLE 6
Preparation of 5-amino-3-cyano-4-(4-chlorophenylsulfonyl)-1-(2,6-dichloro-4-trifluoromethylphenyl)pyrazole Three drops of triethylamine were added to 0.3 g (0.61 mmole) of 2-(4-chlorophenylsulfonyl)-2-(2,6-dichioro-4-trifluoromethyl)phenylazo succinonitrile in 20 mL dichloromethane. After stirring two hours at room temperature the reaction was worked-up by diluting with dichloromethane and partitioning from water. The layers were separated and the aqueous layer was back-extracted once with dichloromethane. The combined organics were dried (Na$_2$SO$_4$) filtered, concentrated and chromatographed through silica gel eluting with 90:10 hexane:ethyl acetate. Isolation gave 0.14 g (47% yield) of the title compound, 100% pure by HPLC as an orange foam, m.p. 90–95° C.

EXAMPLE 7
Preparation of ethyl 2,3-dicyano-2-(2,6-dichloro-4-trifluoromethyl)phenylazo propionate 22.1 Mmole of ethyl dicyanopropionate in 20 mL absolute ethanol was cooled to 0° C., and 20.9 mmole of the hydrogensulfate diazonium salt of 2,6-dichloro-4-trifluoromethylaniline was added via addition funnel over 15 minutes. The reaction was warmed to room temperature and stirred overnight. The reaction was worked-up by adding water and dichloromethane. The layers were separated and the aqueous layer was back extracted once with dichloromethane. The combined organics were washed once with brine and the organic layer was dried ($Na_2SO_4$), filtered, concentrated and chromatographed through silica gel using 90:10 hexane:ethyl acetate. Isolation gave 2.7 g (33%) of the title compound as a red viscous oil which contained 82% desired azo product and 13% of the corresponding hydrazone. $^1H$ NMR ($CDCl_3$) indicated desired product as the major component: δ7.70 (s, 2H), 4.44 (m, 2H), 3.58 (q, 2H), 1.39 (t, 3H).

EXAMPLE 8
Preparation of 5-amino-3-cyano-1-(2,6-dichloro-4-trifluoromethylphenyl)4-carboethoxyprazole To a 100 mL reaction flask was added 0.51 g (1.30 mmole) ethyl 2,3-dicyano-2-(2,6-dichloro-4-trifluoromethyl)phenylazo propionate in 20 mL tetrahydrofuran. The reaction was cooled to −78° C. and 0.52 g (1.30 mmole) sodium hydride (60% dispersion in oil) was added in one portion. The reaction mixture warmed to room temperature overnight. Two grams of silica gel and 40 mL ethyl acetate were added to the reaction mixture and the slurry was concentrated and chromatographed through silica gel eluting with 90:10 hexane:ethyl acetate (1 L) and 80:20 (2 L). Isolation gave 0.16 g (38% yield based on 82% pure starting material), a solid that was 99% pure by HPLC, m.p. 201.5–202.5° C.

EXAMPLE 9
Preparation of Hydrogensulfate Diazonium salt of 2,6-dichloro-4-trifluoromethylaniline To a 100 mL reaction flask was added 5.3 g (23.2 mmole) 2,6-dichloro-4-trifluoromethylaniline dissolved in 45 mL glacial acetic acid. The solution was cooled in an ice water bath and 3.8 g (30.1 mmole) nitrosylsulfuric acid was added in one portion. The reaction was removed from the ice bath and stirred at room temperature for two hours. The resulting diazonium salt was used without purification.

The compounds of formula (IV) prepared by the process of the present invention are useful as pesticides.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. The compound which is:

3-(4-chlorophenylsulfonyl)-3-(2,6-dichloro-4-trifluoromethylphenylazo)-4-cyanobutan-2-one; or 2-(4-chlorophenylsulfonyl)-2-(2,6-dichloro-4-trifluoromethyl)phenylazo succinonitrile.

* * * * *